US008551965B2

(12) United States Patent
McGuigan et al.

(10) Patent No.: US 8,551,965 B2
(45) Date of Patent: *Oct. 8, 2013

(54) ANTI-VIRAL PYRIMIDINE NUCLEOSIDE ANALOGUES

(75) Inventors: Christopher McGuigan, Cardiff (GB); Jan Balzarini, Heverlee (BE)

(73) Assignees: University College Cardiff Consultants Limited, Cardiff (GB); Rega Foundation, Leuven (BE)

(*) Notice: Subject to any disclaimer, the term of this patent is extended or adjusted under 35 U.S.C. 154(b) by 0 days.

This patent is subject to a terminal disclaimer.

(21) Appl. No.: 12/889,980

(22) Filed: Sep. 24, 2010

(65) Prior Publication Data

US 2011/0015147 A1     Jan. 20, 2011

Related U.S. Application Data

(62) Division of application No. 10/257,855, filed as application No. PCT/GB01/01694 on Apr. 12, 2001, now Pat. No. 7,820,631.

(30) Foreign Application Priority Data

Apr. 17, 2000 (GB) .................................. 0009486.2

(51) Int. Cl.
| A61K 31/706 | (2006.01) |
| A61K 31/498 | (2006.01) |
| A61K 31/4985 | (2006.01) |
| C07D 403/02 | (2006.01) |
| C07D 405/04 | (2006.01) |
| C07H 19/23 | (2006.01) |
| C07H 19/24 | (2006.01) |

(52) U.S. Cl.
CPC ............ *A61K 31/706* (2013.01); *A61K 31/498* (2013.01); *A61K 31/4985* (2013.01); *C07D 403/02* (2013.01); *C07D 405/04* (2013.01); *C07H 19/24* (2013.01); *C07H 19/23* (2013.01)
USPC .......... 514/43; 514/49; 514/260.1; 514/265.1; 514/258.1; 536/27.2; 536/27.13; 544/278; 544/280; 544/253

(58) Field of Classification Search
None
See application file for complete search history.

(56) References Cited

U.S. PATENT DOCUMENTS

| 5,430,026 | A | 7/1995 | Hertel et al. |
| 6,444,682 | B1 | 9/2002 | Simmonds et al. |
| 6,455,513 | B1 | 9/2002 | McGuigan et al. |
| 6,573,247 | B1* | 6/2003 | McGuigan et al. ............ 514/43 |
| 7,419,968 | B1 | 9/2008 | Shepard et al. |
| 7,820,631 | B2* | 10/2010 | McGuigan et al. ............ 514/43 |
| 2001/0018440 | A1 | 8/2001 | Chu et al. |
| 2003/0148967 | A1 | 8/2003 | McGuigan et al. |
| 2003/0176370 | A1 | 9/2003 | McGuigan et al. |
| 2008/0070852 | A1 | 3/2008 | Averett et al. |
| 2010/0222295 | A1* | 9/2010 | McGuigan et al. ............ 514/49 |
| 2010/0256087 | A1* | 10/2010 | Balzarini et al. ............. 514/49 |

FOREIGN PATENT DOCUMENTS

| EP | 346108 | 12/1989 |
| JP | 62-255499 | 11/1987 |
| WO | WO-01/07087 | 2/2001 |
| WO | WO-01/07454 | 2/2001 |

OTHER PUBLICATIONS

Silverman, R. The Organic Chemistry of Drug Design and Drug Action, "Chapter 8: Prodrugs and Drug Delivery Systems" Published 1992 by Academic Press, pp. 352-397.*
Wolff. M., "Burger's Medicinal Chemistry and Drug Discovery" published 1994 by John Wiley and Sons, pp. 975-977.*
Testa et al., "Prodrug Research, Futile or Fertile?" Biochemical Pharmacology (2004) vol. 68, pp. 2097-2106.*
Stella, V., "Prodrugs as Therapeutics" Expert Opinion on Therapeutic Patents (2004) vol. 14 No. 3, pp. 277-280.*
U.S. Appl. No. 13/193,343, filed Jul. 2011, McGuigan et al.*
Ettmayer et al., "Lessons Learned from Marketed and Investigational Prodrugs" Journal of Medicinal Chemistry (2004) vol. 47 No. 10, pp. 2393-2404.*
Merriam-Webster's Collegiate Dictionary, Tenth Edition, published 1998 by Merriam-Webster, incorporated, pp. 924 and 935.*
Weller et al, "Pharmacokinetics of the acyclovir pro-drug valaciclovir after escalating single-and multiple-does administration to normal volunteers", Dec. 1993, pp. 595-605, Clinical Pharmacology and Therapeutics.
Jung et al, "Single-dose pharmacokinetics of valanciclovir in HIV- and CMV-seropositive subjects", 1999, pp. 800-804, vol. 39, The Journal of Clinical Pharmacology.
McGuigan et al, "Preclinical Development of the BCMA's: The Most Potent Anti-VZU Agents Reported to Date", Abstract 14, p. A31, in: "Program and Abstracts—The Nineteenth International Conference on Antiviral Research," May 7-11, 2006, published as Antiviral Research vol. 70 (2006) A1-A99.
McGuigan et al, "Phosphoramidate derivatives of d4T with improved anti-HIV efficacy retain full activity in thymidine kinase-deficient cells", May 21, 1996, pp. 1183-1186, vol. 6, No. 10, Bioorganic & Medicinal Chemistry Letters, Oxford, GB.
Angell A et al, "Bicyclic anti-VZV nucleosides: thieno analogues bearing an alkylphenyl side chain have reduced antiviral activity", May 17, 2004, pp. 2397-2399, vol. 14, No. 10, Bioorganic & Medicinal Chemistry Letters, Oxford, GB.

(Continued)

*Primary Examiner* — Eric S Olson
(74) *Attorney, Agent, or Firm* — Mintz Levin Cohn Ferris Glovsky and Popeo, P.C.; Ivor R. Elrifi; Heidi A. Erlacher

(57) ABSTRACT

A compound of formula (I) wherein Ar can be one six-membered or two fused six-membered aromatic rings; $R_8$ and $R_9$ can be hydrogen, alkyl, cycloalkyl, halogens, amino, alkylamino, dialkylamino, nitro, cyano, alkyoxy, aryloxy, thiol, alkylthiol, arythiol, or aryl; Q can be O, S or $CY_2$, where Y may be H, alkyl or halogens; X can be O, NH, S, N-alkyl, $(CHR_2)_m$ where m is 1 to 10, and $CY_2$; Z can be O, S, NH, or N-alkyl; U" is H and U' can be H or $CH_2$; wherein: T can be OH, H, halogens, O-alkyl, O-acyl, O-aryl, CN, $NH_2$, or $N_3$; T' and T" can be H or halogen; and W can be H or a phosphate group. Compounds show anti-viral activity, for example with respect to varicella zoster virus.

7 Claims, No Drawings

(56) References Cited

OTHER PUBLICATIONS

Good et al, "Disposition in the dog and the rat of 2,6-diamino-9-(2-hydroxyethoxymethyl)purine (A134U), a potential prodrug of acyclovir", 1983, pp. 644-651, vol. 227, J. Pharmacol Exp. Ther.

Krenitsky et al, "6-Deoxyacyclovir: a xanthine Oxidase-activated prodrug of acyclovir", 1984, pp. 3209-3213, vol. 81, Proc. Natl Acad. Sci., USA.

Tolstikov et al, "Novel Type of Interaction of 5-Iodopyrimidinonucleosides with Alkynes," *Izv. Akad. Nauk, Ser. Khim.*, (Issue No. 6), 1449-1450 (1992); *Chemical Abstracts*, 118(13), p. 855, Abstract No. 124938m (Mar. 29, 1992).

Tolstikov et al, "New Type of Reaction of 5-Iodopyrimidine Nucleosides with Alkynes," *Izv. Akad. Nauk, Ser. Khim.*, (Issue No. 3), 596-598 (1993); *Chemical Abstracts*, 124(7), p. 1379, Abstract No. 87652q (Feb. 12, 1996).

Morvan et al, "α-Oligodeoxynucleotides Containing 5-Propynyl Analogues of a-Deoxyuridine and a-Deoxy-cytidine: Synthesis and Base Pairing Properties," *Tetrahedron*, 54(1/2), 71-82 (Jan. 1, 1998).

Inoue et al., "Synthesis of Dodecadeoxynucleotides Containing a Pyrrolo[2,3-d]-pyrimidine Nucleoside and Their Base-pairing Ability," *Nippon Kagaku Kaishi* (J. Chern. Soc. Japan, Chemistry and Industrial Chemistry), (Issue No. 7), 1214-1220 (Jul. 1987); *Chemical Abstracts*, 108, Abstract No. 187183a (May 23, 1988).

Crisp, G.T. et al., "Palladium-catalyzed coupling of terminal alkynes with 5-(tribluoromethanesulfonyloxy)pynmldme nucleosides," *J. Org. Chem.*, 1993, 58, 6614-6619 (Issue No. 24).

Cruickshank, K.A. et al., "Oligonucleotide Labelling: A Concise Synthesis of a Modified Thymidine Phosphoramidite," *Tetra.Lett.*, 1988, 29(41), 5221-5224.

De Clercq, E. et al., "Nucleic acid related compounds. 4~. Synthesis and biological activities of 5-alkynyluracil nucleosides," *J. Med. Chem.*, 1983,26(5), 661-666.

Kumar, R. et al., "Synthesis and Properties of 5-(1, 2-Dihaloethyl)-2'-deoxyuridines and Related Analogues," *J. Heterocyclic Chem.*, 1991,28, 1917-1925 (Dec. 1991).

Kumar, R. et al., "Synthesis of 5-{1-azidovinyl) and 5-{2--(1-azirinyl)] analogs of 2'-deoxyuridine," *Can. J. Chem.*,1996, 74, 1609-1615.

Robins, M.J. et al., "Nucleic acid related compounds. 39. Efficient conversion of 5-iodo to 5-alkynyl and derived 5-substituted uracil bases and nucleosides," *J. Org. Chem.*, 1983,48, 1854-1862 (Issue No. 11).

Robins, M.J. et al., "Nucleic Acid Related Compounds. 31. Smooth and Efficient Palladium-Copper Catalyzed Coupling of Terminal Alkynes with 5-Iodouracil Nucleosides," *Tetra. Lett.* 1981,22,421-424.

Woo, J. et al., "G/C-modified oligodeoxynucleotides with selective complementarity: synthesis and hybridization properties," *Nucl. Acids Res.*, 1996,24(13),2470-2475.

\* cited by examiner

ANTI-VIRAL PYRIMIDINE NUCLEOSIDE ANALOGUES

CROSS REFERENCE TO RELATED APPLICATIONS

The present application is a divisional application of U.S. application Ser. No. 10/257,855, filed Oct. 17, 2002, which is a National Stage application of International application PCT/GB01/01694, filed Apr. 12, 2001, which claims the benefit of United Kingdom patent application GB 0009486.2, filed Apr. 12, 2000, all of said applications incorporated herein by reference.

FIELD OF THE INVENTION

The present invention relates to a class of nucleoside analogues and to their therapeutic use in the prophylaxis and treatment of viral infection for example by varicella zoster virus (VZV). Varicella zoster virus is the aetiological agent in chickenpox and shingles which can cause considerable human illness and suffering.

BACKGROUND OF THE INVENTION

The following references and other information are pertinent to the background of the invention:

WO 98/49177 describes a class of nucleoside analogues demonstrating anti-viral properties. A representative of the compounds disclosed in WO 98/49177 is 3-(2-deoxy-β-D-ribofuranosyl)-6-decyl-2,3-dihydrofuro [2,3-d]pyrimidin-2-one.

"Acyclovir" is a compound known to have anti-viral properties. It is described in The Merck Index 12th Edition.

BVDU is (E)-5-(2-bromo-vinyl)-2'-deoxyuridine and is described in De Clercq et al. Proc. Natl. Acad. Sci., USA 1979, 76, 2947.

G. T. Crisp and B. L. Flynn, J. Org. Chem. 1993, 58, 6614 describes palladium catalyzed couplings of terminal alkynes with a variety of oxyuridines. One coupling described is that between 5-ethynyl-2-deoxyuridine and a range of fluorinated aryl compounds.

E. V. Malakhova et al. Bioorg. Khim. (1998), 24 (9), 688-695 describes reagents for introducing a fluorescent deoxyuridine 2-phenylbenzoxazole derivative into oligonucleotides.

SUMMARY OF THE INVENTION

It is the object of the present invention to provide a novel class of nucleoside analogues.

It is a further object of the present invention to provide a class of nucleoside analogues for therapeutic use in the prophylaxis and treatment of a viral infection, for example a varicella zoster virus (VZV).

According to the first aspect of the present invention there is provided a compound having formula I as follows:

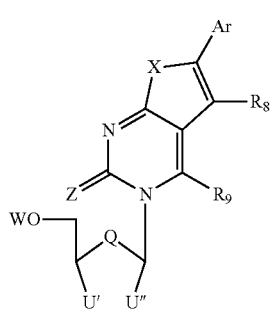

(I)

wherein:

Ar is an, optionally substituted, aromatic ring system, the aromatic ring system comprising one six-membered aromatic ring or two fused six-membered aromatic rings;

$R_8$ and $R_9$, are each independently selected from H, alkyl, aryl, cycloalkyl, halogen, amino, nitro, thiol, cyano, alkylamino, dialkylamino, alkoxy, aryloxy, alkylthiol, and arylthiol;

Q is selected from the group comprising O, S, and $CY_2$, where Y may be the same or different and is selected from H, alkyl, and halogen;

X is selected from the group comprising O, NH, S, N-alkyl, $(CH_2)_m$ where m is 1 to 10, and $CY_2$, where Y may be the same or different and is selected from H, alkyl, and halogen;

Z is selected from the group comprising O, S, NH, and N-alkyl;

U" is H and U' is selected from H and $CH_2T$, or U' and U" are joined so as to provide a ring moiety including Q wherein U'—U" together is respectively selected from the group comprising CT'H-CT'T" and CT'=CT', so as to provide the following ring moiety options:

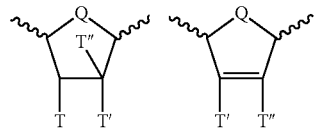

wherein T is selected from the group comprising OH; H, halogens, O-alkyl, O-acyl, O-aryl, CN, $NH_2$, and $N_3$;

T' is selected from the group comprising H and halogens and where more than one T' is present, they may be the same or different;

T" is selected from the group comprising H and halogens; and

W is selected from the group comprising H, a phosphate group, and a phosphonate group; with the proviso that when T is OAc and T' and T" are present and are H, Ar is not 4-(2-benzoxazolyl)phenyl.

It is to be understood that the present invention extends to compounds according to formula I wherein the group W is modified to provide any pharmacologically acceptable salt or derivative of H, phosphate, or phosphonate. The present invention also includes any compound which is a pro-drug of the compound according to formula (I), any such prodrug being provided by modification of the moiety W, wherein W is selected from phosphates and derivatives thereof, and phosphonates and derivatives thereof.

The aromatic ring system present in Ar may contain one, two, three or four suitable ring heteroatoms, whose position may be varied. Any ring heteroatoms present may be the same or different and can, for example, be O, S or N.

Preferably the aromatic ring system in Ar is carbocyclic. The aromatic ring system in Ar is thus preferably selected from the group comprising, optionally substituted, phenyl and naphthyl radicals. More preferably, the aromatic ring system in Ar comprises one six-membered carbocyclic ring and is thus phenyl or a substituted derivative of phenyl.

When the aromatic ring system is naphthyl or a substituted derivative of naphthyl, the naphthyl radical is preferably bonded to the nucleoside ring system at a position adjacent the fused bond in the naphthyl radical.

Preferably the aromatic ring system in Ar is substituted. Preferably the aromatic ring system in Ar is substituted by one or more moieties independently selected from the group comprising H, alkyl, aryl, and cycloalkyl, chlorine, bromine, iodine, cyano, alkylamino, dialkylamino, alkoxy, aryloxy, alkylthiol and arylthiol. Suitable moieties for use as substituents on the aromatic ring system of Ar include $C_1$-$C_{10}$ alkyl, $C_3$-$C_{10}$ cycloalkyl, $C_1$-$C_{10}$ alkylamino, $C_3$-$C_{10}$ dialkylamino, $C_1$-$C_{10}$ alkoxy, $C_6$-$C_{10}$ aryloxy, $C_1$-$C_{10}$ alkylthiol, and $C_6$-$C_{10}$ aryl.

Any alkyl, cycloalkyl, aryl or alkoxy substituents on the aromatic ring system of Ar may themselves be substituted. Preferably such substituents on the said alkyl, cycloalkyl, aryl and alkoxy substituents comprise one or more members independently selected from the group comprising chlorine, bromine, iodine, CN, $CO_2$ alkyl ($C_1$ to $C_6$), $CONH_2$, CONH alkyl ($C_1$ to $C_6$), SH, S alkyl ($C_1$ to $C_6$) and $NO_2$.

Preferably any substituent present in or on the aromatic ring system of Ar is at least substantially non-polar. Preferably any such substituent is hydrophobic.

Preferably any substituent or substituents on the aromatic ring system of the Ar comprise one or more alkoxy moieties and/or one or more, optionally substituted, alkyl moieties.

Any alkyl or alkoxy moiety present on the aromatic ring system of Ar is preferably straight chained, unsubstituted and saturated. Branched, substituted and/or unsaturated alkyl or alkoxy groups may however be employed. The term 'alkyl' with respect to any substituent present on the aromatic ring system thus comprises any aliphatic non-cyclic hydrocarbyl radical, including alkenyl and alkynyl. The nature, position, and number of any substituents and unsaturation may be varied.

Preferably any such alkyl or alkoxy moiety or moieties, in total, comprise 3 to 8 carbon atoms, calculated excluding any substituents that may be present on the said alkyl or alkoxy moiety or moieties. The remainder of any substituent positions on the aromatic ring system of Ar are preferably H. More preferably any alkyl moiety or moieties present on the aromatic ring system of Ar comprise, in total, from 4 to 7 carbon atoms, even more preferably from 5 to 6 carbon atoms, calculated excluding any substituents that may be present on the said alkyl moiety or moieties. More preferably any alkoxy moiety or moieties present on the aromatic ring system of Ar comprise, in total, from 3 to 7 carbon atoms, calculated excluding any substituents that be present on the said alkoxy or alkoxy moieties.

Any alkyl moiety or moieties present on the aromatic ring system of Ar is preferably selected from the group comprising $C_1$, $C_2$, $C_3$, $C_4$, $C_5$, $C_6$, $C_7$, and $C_8$ alkyl moieties and mixtures thereof, more preferably from the group comprising $C_3$, $C_4$, $C_5$, $C_6$, $C_7$ and $C_8$ alkyl moieties and mixtures thereof, even more preferably from the group comprising $C_4$, $C_5$, $C_6$ and $C_7$ alkyl moieties and mixtures thereof. Preferably an alkyl moiety or moieties is selected from the group comprising $C_5$ and $C_6$ alkyl moieties and mixtures thereof.

Where the substituent present on the aromatic ring system is an aryl moiety, it is preferably phenyl. Such aryl substituents can be substituted. Preferably any such substituents are selected from the group set out above.

Any substituent on the aromatic ring system of Ar can be at any position. Any of the meta, ortho or para positions can therefore be occupied by a substituent. Preferably any single substituent, particularly where the aromatic ring system comprises a phenyl derivative, is a para substituent with respect to the bond between the aromatic ring system and the nucleoside fused ring system. Preferably the aromatic ring system of Ar is a six-membered carbocyclic ring system and comprises one alkyl or one alkoxy substituent at the para position.

Each of $R_8$ and $R_9$ may be substituted or unsubstituted, and may be branched or unbranched as appropriate to their structure. When either of $R_8$ and $R_9$ are alkyl or cycloalkyl they may be saturated or unsaturated. The nature, position, and number of any substituents and unsaturation present may be varied.

When either of $R_8$ and $R_9$ is alkyl or cycloalkyl, suitable substituents that may optionally be present include OH, halogen, amino, CN, $CO_2H$, $CO_2$ alkyl, $CONH_2$, CONH alkyl, SH, S alkyl, and $NO_2$, wherein alkyl in a substituent is suitably $C_1$-$C_6$. Suitably, any substituent is non-polar, more suitably any such substituent is hydrophobic.

Suitably $R_8$ is selected from the group comprising H, $C_1$-$C_{10}$ alkyl, $C_3$-$C_{10}$ cycloalkyl, $C_1$-$C_{10}$ alkylamino, $C_1$-$C_{10}$ dialkylamino, $C_1$-$C_{10}$ alkyloxy, $C_6$-$C_{10}$ aryloxy, $C_1$-$C_{10}$ alkylthiol, and $C_6$-$C_{10}$ aryl.

Suitably $R_9$ is selected from the group H, $C_1$-$C_{10}$ alkyl, $C_3$-$C_{10}$ cycloalkyl, $C_1$-$C_{10}$ alkylamino, $C_1$-$C_{10}$ dialkylamino, $C_1$-$C_{10}$ alkyloxy, $C_6$-$C_{10}$ aryloxy, $C_1$-$C_{10}$ alkylthiol, and $C_6$-$C_{10}$ aryl.

Preferably each of $R_8$ and $R_9$ is a small alkyl, ie. a $C_1$-$C_2$ alkyl group, or H. More preferably, each of $R_8$ and $R_9$ is H.

Throughout the present specification, 'halogen' is taken to include F, Cl, Br and I. Unless otherwise stated, chlorine and bromine are preferred.

Unless otherwise stated, throughout the present specification 'alkyl' is taken to include $C_1$-$C_{10}$ alkyl, preferably $C_1$-$C_5$ alkyl, and saturated and unsaturated, branched and unbranched, and substituted and unsubstituted aliphatic hydrocarbyl.

Unless otherwise stated, throughout the present specification 'cycloalkyl' is taken to include $C_3$-$C_{10}$, preferably $C_5$-$C_8$, and saturated and unsaturated and substituted and unsubstituted cyclic aliphatic hydrocarbyl.

Unless otherwise stated, throughout the present specification 'aryl' is taken to include $C_5$-$C_{10}$ single ring or fused bi-ring aryl, substituted and unsubstituted aryl, and aryl containing 1 to 4 heteroatoms, which may be the same or different and may be selected from, for example, O, N and S.

Suitable substituents for 'alkyl', 'cycloalkyl' and 'aryl', other than when an alkyl, cycloalkyl or aryl moiety is present as a substituent on the aromatic ring system in Ar, include one or more members independently selected from the group comprising OH, halogen, amino, CN, $CO_2H$, $CO_2$ alkyl($C_1$ to $C_6$), $CONH_2$, CONH alkyl($C_1$ to $C_6$), SH, S alkyl($C_1$ to $C_6$) and $NO_2$.

Preferably Q is $CH_2$, S, or O. More preferably Q is O. Where Q is $CY_2$ and includes a halogen, it is preferably F. Y is preferably H.

Preferably X is O, S, or NH. More preferably X is O. Where X is $(CH)_n$, n is preferably 1 or 2, most preferably 1. Suitably, when X is N-alkyl, alkyl is $C_1$-$C_5$, and when X is $CY_2$, at least one Y is $C_1$-$C_5$ alkyl. Most preferably, X is O.

Preferably Z is O. Where Z is N-alkyl, suitably the alkyl is $C_1$-$C_5$.

Preferably U' and U" are joined to provide the saturated ring moiety including T, T' and T". Preferably T, T', and T" in such a ring moiety are respectively OH, H, and H.

Preferably T is OH. When T is halogen it is preferably F.

Preferably each of T' and T" is H. When either or both of T' and T" is halogen, it is preferably F.

When W is a moiety which renders the compound a pro-drug of the compound according to Formula (I) it is to be understood that the term pro-drug includes the corresponding free base of each of the nucleosides described.

It is also to be understood that the term 'phosphate' includes diphosphates and triphosphates. Hence, W includes pharmacologically acceptable salts and derivatives of phosphates, diphosphates, and triphosphates, and of phosphonates, diphosphonates, and triphosphonates. It also includes any moiety which provides a compound which is a prodrug of the compound according to formula (I), wherein W is selected from phosphates, diphosphates, and triphosphates, and derivatives thereof, and phosphonates, diphosphonates, and triphosphonates, and derivatives thereof.

Each compound of the present invention may be a pure stereoisomer coupled at each of its chiral centers or it may be inverted at one or more of its chiral centers. It may be a single stereoisomer or a mixture of two or more stereoisomers. If it is a mixture the ratio may or may not be equimolar. Preferably the compound is a single stereoisomer. The compound may be in either enantiomeric form i.e. it may be either the D or L enantiomer either as a single stereoisomer or as a mixture of the two enantiomers. More preferably the compounds has a stereochemistry resembling natural deoxy nucleosides derived from β-D-2-deoxyribose. However other enantiomers particularly the L enantiomers may be employed.

It is to be understood that the present invention extends to compounds wherein the sugar moiety and phosphate if present have either together or separately been modified as well known to a person skilled in art. For example the sugar substituent on the nucleoside may be usefully phosphonated.

It is also possible for a compound embodying the present invention to be in a sugar form as for example modified and derived from a D-xylo sugar system.

Particularly preferred compounds embodying the present invention have the following formulae:

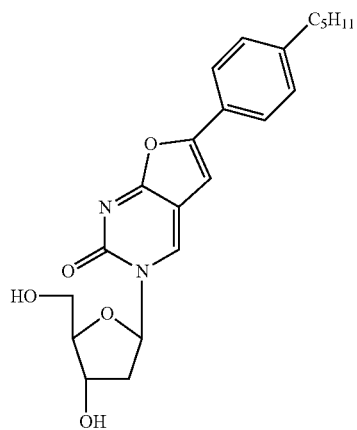

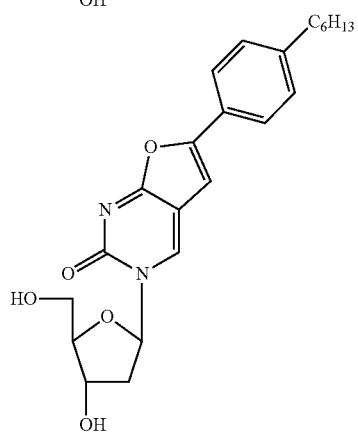

According to a further aspect of the present invention there is provided a method for preparing compounds having Formula I above wherein a 5-halo nucleoside analogue is contracted with a terminal alkyne in the present of a catalyst. Alternatively 5-alkynyl nucleoside can be cyclized in the presence of a catalyst. Suitably the catalyst is a copper catalyst. The 5-alkynyl nucleoside has the general formula:

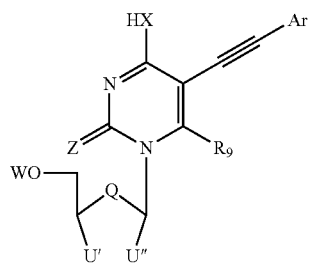

Compounds embodying the present invention can show antiviral activity. In particular it has surprisingly been found that compounds embodying the present invention can show antiviral activity against for example varicella zoster virus.

According to a further aspect of the present invention there is provided a compound according to the present invention for use in a method of treatment, suitably in the prophylaxis or treatment of a viral infection.

According to a further aspect of the present invention there is provided use of a compound according to the present invention in the manufacture of a medicament for the prophylaxis or treatment of viral infection.

According to a further aspect of the present invention there is provided a method of prophylaxis or treatment of viral infection comprising administration to a patient in need of such treatment an effective dose of a compound according to the present invention According to a further aspect of the present invention there is provided use of a compound of the present invention in the manufacture of a medicament for use in the prophylaxis or treatment of a viral infection, particularly an infection with the varicella zoster virus.

According to a further aspect of the present invention there is provided a pharmaceutical composition comprising a compound of the present invention in combination with a pharmaceutically acceptable excipient.

Medicaments embodying the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, compounds embodying the present invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, compounds embodying the present invention will generally be provided in sterile aqueous solutions or suspensions, buffered to an appropriate pH and isotonicity. Suitable aqueous vehicles include Ringer's solution and isotonic sodium chloride. Aqueous suspensions embodying the invention may include suspending agents such as cellulose derivatives, sodium alginate, polyvinyl-pyrrolidone and gum tragacanth, and a wetting agent such as lecithin.

Suitable preservatives for aqueous suspensions include ethyl and n-propyl phydroxybenzoate.

Compounds embodying the present invention can be presented as liposome formulations.

In general, a suitable dose will be in the range of 0.001 to 300 mg per kilogram body weight of the recipient per day, preferably in the range of 0.01 to 25 mg per kilogram body weight per day and most preferably in the range 0.05 to 10 mg per kilogram body weight per day. The desired dose is preferably presented as two, three, four, five or six or more sub-doses administered at appropriate intervals throughout the day. These sub-doses may be administered in unit dosage forms, for example, containing 0.1 to 1500 mg, preferably 0.2 to 1000 mg, and most preferably 0.5 to 700 mg of active ingredient per unit dosage form.

Embodiments of the present invention will now be described by way of example only.

EXAMPLE 1

Preparation of 3-(2'-deoxy-β-D-ribofuranosyl)-6-(4-n-propylphenyl)-2,3-dihydrofuro-[2,3-d]pyrimidin-2-one

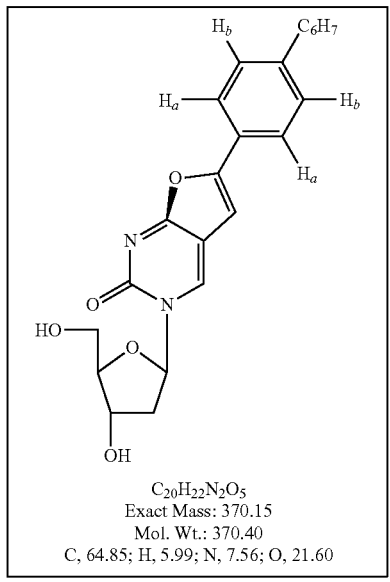

$C_{20}H_{22}N_2O_5$
Exact Mass: 370.15
Mol. Wt.: 370.40
C, 64.85; H, 5.99; N, 7.56; O, 21.60

To a solution of 5-(4-n-propyl-phenylacetylene)-2'-deoxyuridine (200 mg, 0.54 mmol) in methanol and triethylamine (7:3) (20 ml), was added copper iodide (20 mg, 0.102 mmol). The mixture was refluxed for 4 hours. The solvent was removed in vacuo, and the crude product as purified by flash column chromatography (initial eluent: ethyl acetate, followed by: ethyl acetate/methanol (9:1)). The combined fractions were combined and the solvent was removed in vacuo to give the crude product, which was recrystallized from methanol to give pure 3-(2'-deoxy-β-D-ribofuranosyl)-6-(4-n-propylphenyl)-2,3-dihydrofuro-[2,3-d]pyrimidin-2-one (86 mg, 43%).

$^1$H-NMR (d$_6$-DMSO; 300 MHz); 8.72 (1H, s, H-4), 7.43 (2H, H$_a$) −7.28 (2H, H$_b$) (AB system, $^3$J=7.89 Hz, $^4$J=2.3 Hz), 7.15 (1H, s, H-5), 6.18 (1H, dd, $^3$J=6.15 Hz, H-1'), 5.31 (1H, d, $^3$J=4.0 Hz, 3'-OH), 5.12 (1H, t, $^3$J=5.01 Hz, 5'-OH), 4.31 (1H, m, H-3'), 3.89 (1H, m, H-4'), 3.51 (2H, m, 2.65 (2H, t, $^3$J=6.9 Hz, α-CH$_2$), 2.31 and 2.12 (2H, m, 2-H'a and 2-H'b), 1.58 (2H, sxt, CH$_2$, $^3$J=6.9 Hz), 0.85 (3H, t, $^3$J=6.9 Hz, CH$_3$).
$^{13}$C-NMR (d$_6$-DMSO; 75 MHz): 13.2 (CH$_3$), 20.1, 22.3, (C$_2$H$_4$), 41.5 (C-2'), 62.3 (C-5'), 71.6 (C-3'), 83.2, 88.4 (C-1', C-4'), 100.4 (C-5), 104.6 (C-4a), 125.3 (C—H$_b$), 128.4 (ipso-C), 131.8 (C—H$_a$), 141.2 (para-C), 138.5 (C-4), 154.6 (C-6), 159.1 (C-2), 172.3 (C-7a).

General Procedure for the preparation of 3-(2'-deoxy-β-D-ribofuranosyl)-6-(4n-alkylphenyl)-2,3-dihydrofuro-[2,3-d]pyrimidin-2-one analogues To a stirred solution of 5-iodo-2'-deoxyuridine (800 mg, 2.26 mmol) in anhydrous dimethylformamide (8 ml), was added diisopropylethylamine (584 mg, 0.8 ml, 4.52 mmol), the 4-n-alkyl-phenylacetylene (6.76 mmol), tetrakis (triphenylphoshine) palladium (0) (261 mg, 0.266 mmol) and copper (I) iodide (86 mg, 0.452 mmol). The mixture was stirred for 18 hours, at room temperature, under a nitrogen atmosphere, after which time tlc (ethyl acetate/methanol 9:1), showed complete conversion of the starting material. Copper (I) iodide (80 mg, 0.40 mmol), triethylamine (15 ml) and methanol (20 ml) were then added to the mixture, which was subsequently refluxed for 4 hours. The reaction mixture was then concentrated in vacuo, and the resulting residue was dissolved in dichloromethane and methanol (1:1) (6 ml), whereupon an excess of Amberlite IRA-400 (HCO3 form) was added and stirred for 30 minutes. The resin was filtered and washed with methanol, and the combined filtrate was evaporated to dryness. The crude product was purified by flash column chromatography (Initial eluent: ethyl acetate, followed by: ethyl acetate/methanol (9:1)). The appropriate fractions were combined, where the solvent was removed in vacuo, to give the pure product.

EXAMPLE 2

Preparation of 3-(2'-deoxy-β-D-ribofuranosyl)-6-(4n-butylphenyl)-2,3-dihydrofuro-[2,3-d]pyrimidin-2-one

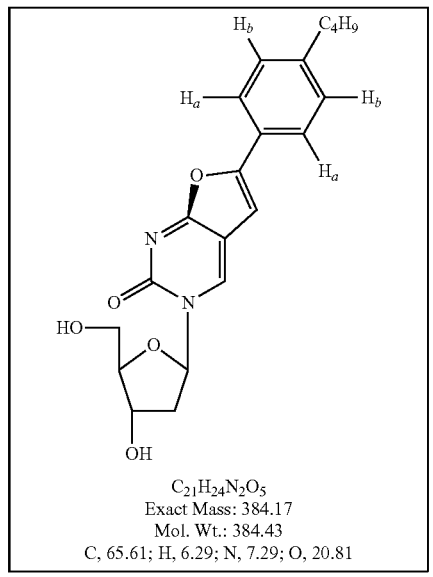

$C_{21}H_{24}N_2O_5$
Exact Mass: 384.17
Mol. Wt.: 384.43
C, 65.61; H, 6.29; N, 7.29; O, 20.81

The above general procedure was carried out using 4-n-butyl-phenylacetylene (1.072 g, 6.76 mmol), which gave 3-(2'-deoxy-β-D-ribofuranosyl)-6-(4-n-butylphenyl)-2,3-dihydrofuro-[2,3-d]pyrimidin-2-one (140 mg, 16%), after purification by column chromatography.

$^1$H-NMR (d$_6$-DMSO; 300 MHz); 8.76 (1H, s, H-4), 7.46 (2H, H$_a$) –7.31 (2H, H$_b$) (AB system, $^3$J=7.89 Hz, $^4$J=2.3 Hz), 7.20 (1H, s, H-5), 6.21 (1H, dd, $^3$J=6.15 Hz, H-1'), 5.37 (1H, d, $^3$J=4.0 Hz, 3'-OH), 5.31 (1H, t, $^3$J=5.01 Hz, 5'-OH), 4.31 (1H, m, H-3'), 3.75 (1H, m, H-4'), 3.48 (2H, m, H-5'), 2.65 (2H, t, $^3$J=6.9 Hz, α-CH$_2$), 2.31 and 2.12 (2H, m, 2-H'a and 2-H'b), 1.62 (4H, m, CH$_2$), 0.87 (3H, t, $^3$J=6.9 Hz, CH$_3$). $^{13}$C-NMR (d$_6$-DMSO; 75 MHz): 13.2 (CH$_3$), 20.1, 22.3, 27.9 (C$_3$H$_6$), 42.5 (C-2'), 63.7 (C-5'), 73.6 (C-3'), 83.5, 88.7 (C-1', C-4'), 100.8 (C-5), 108.4 (C-4a), 125.3 (C—H$_b$), 128.4 (ipso-C), 131.8 (C—H$_a$), 141.2 (para-C), 138.5 (C-4), 154.6 (C-6), 159.1 (C-2), 170.9 (C-7a).

EXAMPLE 3

Preparation of 3-(2'-deoxy-β-D-ribofuranosyl)-6-(4-n-pentylphenyl)-2,3-dihydrofuro-[2,3-d]pyrimidin-2-one

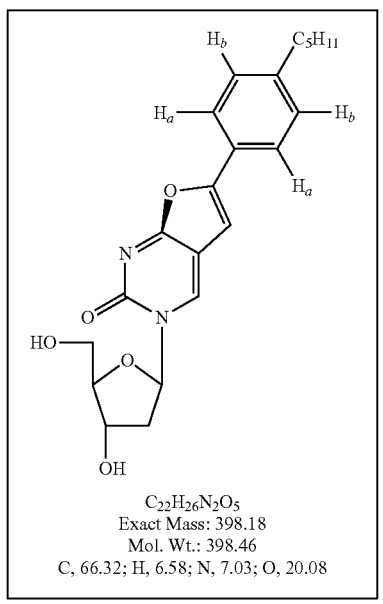

C$_{22}$H$_{26}$N$_2$O$_5$
Exact Mass: 398.18
Mol. Wt.: 398.46
C, 66.32; H, 6.58; N, 7.03; O, 20.08

The above general procedure was carried out using 4-n-pentyl-phenyllacetylene (1.15 g, 6.76 mmol), which gave 3-(2'-deoxy-β-D-ribofuranosyl)-6-(4-n-pentylphenyl)-2,3-dihydrofuro-[2,3-d]pyrimidin-2-one (137 mg, 15%), after purification by column chromatography.

$^1$H-NMR (d$_6$-DMSO; 300 MHz); 8.81 (1H, s, H-4), 7.51 (2H, H$_a$) –7.35 (2H, H$_b$) (AB system, $^3$J=7.89 Hz, $^4$J=2.3 Hz), 7.18 (1H, s, H-5), 6.23 (1H, dd, $^3$J=6.15 Hz, H-1'), 5.37 (1H, d, $^3$J=4.0 Hz, 3'-OH), 5.31 (1H, t, $^3$J=5.01 Hz, 5'-OH), 4.34 (1H, m, H-3'), 3.79 (1H, m, H-4'), 3.41 (2H, m, H-5'), 2.67 (2H, t, $^3$J=6.9 Hz, α-CH$_2$), 2.34 and 2.14 (2H, m, 2-H'a and 2-H'b), 1.67 (2H, m, CH$_2$), 1.51-1.32 (4H, m, CH$_2$), 0.84 (3H, t, $^3$J=6.9 Hz, CH$_3$). $^{13}$C-NMR (d$_6$-DMSO; 75 MHz): 13.2 (CH$_3$), 20.1, 22.3, 27.9, 28.4, (C$_4$H$_8$), 41.3 (C-2'), 62.6 (C-5'), 71.8 (C-3'), 83.4, 86.4 (C-1', C-4'), 100.4 (C-5), 107.4 (C-4a), 125.4 (C—H$_b$), 127.4 (ipso-C), 131.8 (C—H$_a$), 138.5 (C-4), 141.3 (para-C), 154.6 (C-6), 161.1 (C-2), 170.9 (C-7a).

EXAMPLE 4

Preparation of 3-(2'-deoxy-β-D-ribofuranosyl)-6-(4-n-hexylphenyl)-2,3 dihydrofuro-[2,3-d]pyrimidin-2-one

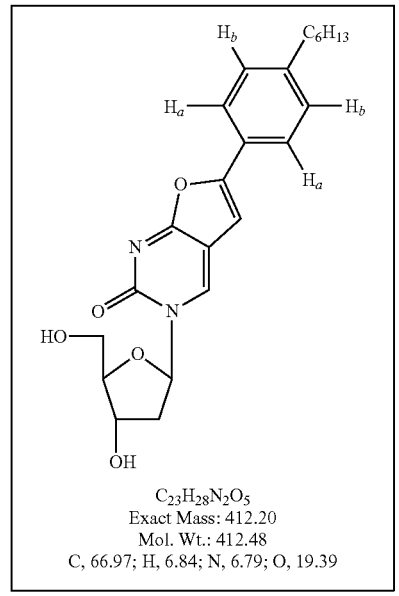

C$_{23}$H$_{28}$N$_2$O$_5$
Exact Mass: 412.20
Mol. Wt.: 412.48
C, 66.97; H, 6.84; N, 6.79; O, 19.39

The above general procedure was carried out using 4-n-hexyl-phenylacetylene (1.25 g, 6.76 mmol), which gave 3-(2'-deoxy-β-D-ribofuranosyl)-6-(4-n-hexylphenyl)-2,3-dihydrofuro-[2,3-d]pyrimidin-2-one (124 mg, 13%), after purification by column chromatography.

$^1$H-NMR (d$_6$-DMSO; 300 MHz); 8.85 (1H, s, H-4), 7.53 (2H, H$_a$) –7.29 (2H, H$_b$) (AB system, 3J=7.89 Hz, $^4$J=2.3 Hz), 7.23 (1H, s, H-5), 6.24 (1H, dd, $^3$J=6.15 Hz, H-1'), 5.58 (1H, d, $^3$J=4.0 Hz, 3'-OH), 5.29 (1H, t, $^3$J=5.01 Hz, 5'-OH), 4.54 (1H, m, H-3'), 3.79 (1H, m, H-4'), 3.51 (2H, m, H-5'), 2.72 (2H, t, $^3$J=6.9 Hz, α-CH$_2$), 2.31 and 2.10 (2H, m, 2-H'a and 2-H'b), 1.62 (2H, m, CH$_2$), 1.42-1.22 (6H, m, CH$_2$), 0.87 (3H, t, $^3$J=6.9 Hz, CH$_3$). $^{13}$C-NMR (d$_6$-DMSO; 75 MHz): 13.2 (CH$_3$), 20.1, 22.3, 27.9, 29.5, 30.2 (C$_5$H$_{10}$), 41.6 (C-2'), 62.3 (C-5'), 769.8 (C-3'), 83.5, 88.7 (C-1', C-4'), 99.1 (C-5), 107.2 (C-4a), 124.3 (C—$H_b$), 126.4 (ipso-C), 129.3 (C—$H_a$), 138.5 (C-4), 141.2 (para-C), 154.6 (C-6), 160.9 (C-2), 171.3 (C-7a).

EXAMPLE 5

Preparation of 3-(2'-deoxy-β-D-ribofuranosyl)-6-(4-n-heptylphenyl)-2,3-dihydrofuro-[2,3-d]pyrimidin-2-one

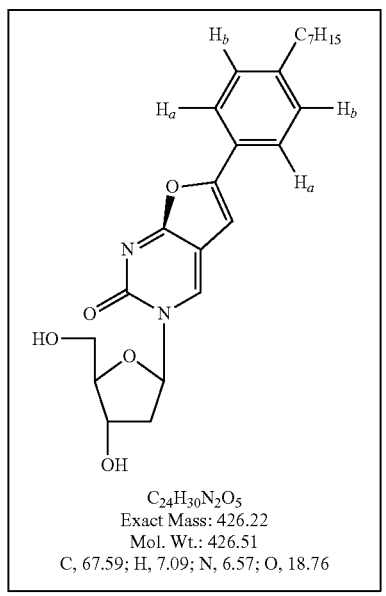

$C_{24}H_{30}N_2O_5$
Exact Mass: 426.22
Mol. Wt.: 426.51
C, 67.59; H, 7.09; N, 6.57; O, 18.76

The above general procedure was carried out using 4-n-heptyl-phenylacetylene (1.25 g, 6.76 mmol), which gave 3-(2'-deoxy-β-D-ribofuranosyl)-6-(4-n-heptylphenyl)-2,3-dihydrofuro-[2,3-d]pyrimidin-2-one (129 mg, 13%), after purification by column chromatography.

$^1$H-NMR ($d_6$-DMSO; 300 MHz); 8.91 (1H, s, H-4), 7.62 (2H, $H_a$) –7.35 (2H, $H_b$) (AB system, $^3J$=7.89 Hz, $^4J$=2.3 Hz), 7.26 (1H, s, H-5), 6.28 (1H, dd, $^3J$=6.17 Hz, H-1'), 5.62 (1H, d, $^3J$=4.1 Hz, 3'-OH), 5.32 (1H, t, $^3J$=5.12 Hz, 5'-OH), 4.52 (1H, m, 3.81 (1H, m, H-4'), 3.62 (2H, m, H-5'), 2.71 (2H, t, $^3J$=6.9 Hz, α-$CH_2$), 2.35 and 2.14 (2H, m, 2-H'a and 2-H'b), 1.59 (2H, m, $CH_2$), 1.48-1.21 (8H, m, $CH_2$), 0.82 (3H, t, $^3J$=6.9 Hz, $CH_3$). $^{13}$C-NMR ($d_6$-DMSO; 75 MHz): 13.2 ($CH_3$), 20.1, 22.3, 27.9, 28.5, 29.5, 30.2 ($C_6H_{12}$), 41.6 (C-2'), 61.5 (C-5'), 69.8 (C-3'), 87.9, 88.5 (C-1', C-4'), 99.1 (C-5), 107.2 (C-4a), 124.3 (C—$H_b$), 126.2 (ipso-C), 129.3 (C—$H_a$), 138.2 (C-4), 144.2 (para-C), 154.6 (C-6), 160.7 (C-2), 170.6 (C-7a).

EXAMPLE 6

Preparation of 3-(2'-deoxy-β-D-ribofuranosyl)-6-(4-n-octylphenyl)-2 3-dihydrofuro-[2,3-d]pyrimidin-2-one

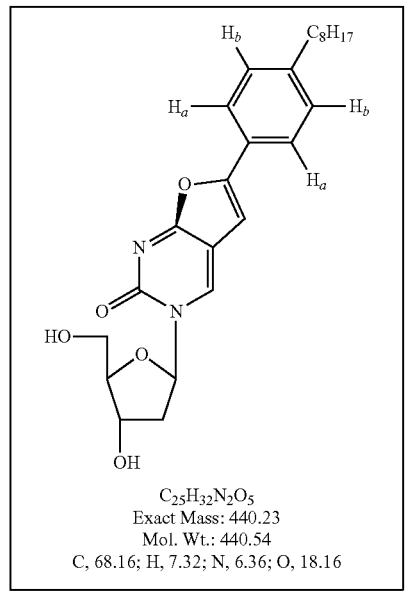

$C_{25}H_{32}N_2O_5$
Exact Mass: 440.23
Mol. Wt.: 440.54
C, 68.16; H, 7.32; N, 6.36; O, 18.16

The above general procedure was carried out using 4-n-octyl-phenylacetylene (1.45 g, 6.76 mmol), which gave 3-(2'-deoxy-β-D-ribofuranosyl)-6-(4-n-octylphenyl)-2,3-dihydro-furo[2,3-d]pyrimidin-2-one (111 mg, 11%), after purification by column chromatography.

$^1$H-NMR ($d_6$-DMSO; 300 MHz); 8.92 (1H, s, H-4), 7.61 (2H, $H_a$) –7.33 (2H, $H_b$) (AB system, $^3J$=7.89 Hz, $^4J$=2.3 Hz), 7.25 (1H, s, H-5), 6.21 (1H, dd, $^3J$=6.19 Hz, H-1'), 5.59 (1H, d, $^3J$=4.1 Hz, 3'-OH), 5.272 (1H, t, $^3J$=5.12 Hz, 5'-OH), 4.39 (1H, m, H-3'), 3.75 (1H, m, 3.62 (2H, m, H-5'), 2.71 (2H, t, $^3J$=6.9 Hz, α-$CH_2$), 2.34 and 2.13 (2H, m, 2-H'a and 2-H'b), 1.61 (2H, m, $CH_2$), 1.51-1.19 (10H, m, $CH_2$), 0.82 (3H, t, $^3J$=6.9 Hz, $CH_3$). $^{13}$C-NMR ($d_6$-DMSO; 75 MHz): 13.2 ($CH_3$), 20.1, 21.39, 22.3, 27.9, 28.5, 29.5, 30.2 ($C_7H_{14}$), 41.7 (C-2'), 61.1 (C-5'), 69.8 (C-3'), 87.9, 88.7 (C-1', C-4'), 99.0 (C-5), 107.2 (C-4a), 124.8 (C—$H_b$), 126.2 (ipso-C), 129.3 (C—$H_a$), 138.2 (C-4), 144.2 (para-C), 154.2 (C-6), 160.7 (C-2), 171.6 (C-7a).

EXAMPLES 7 TO 10 AND 13

The above general procedure was carried out using the appropriate starting materials to produce each of the following respective compounds:

EXAMPLE 7

3-(2'-deoxy-β-D-ribofuranosyl)-6-(phenyl)-2,3-dihydrofuro-[2,3-d]pyrimidin-2-one

EXAMPLE 8

3-(2'-deoxy-β-D-ribofuranosyl)-6-(4-methylphenyl)-2,3-dihydrofuro-[2,3-d]pyrimidin-2-one

EXAMPLE 9

3-(2'-deoxy-β-D-ribofuranosyl)-6-(4-ethylphenyl)-2,3-dihydrofuro-[2,3-d]pyrimidin-2-one

EXAMPLE 10

3-(2'-deoxy-β-D-ribofuranosyl)-6-(4-fluorophenyl)-2,3-dihydrofuro-[2,3-d]pyrimidin-2-one

EXAMPLE 13

3-(2'-deoxy-β-D-ribofuranosyl)-6-(4-phenylphenyl)-2,3-dihydrofuro-[2,3-d]pyrimidin-2-one General Procedure for the preparation of 3-(2'-deoxy-β-D-ribofuranosyl)-6-(4-n-alkoxyphenyl)-2 3-dihydrofuro-[2,3-d]pyrimidin-2-one and 3-(2'-deoxy-β-D-ribofuranosyl)-6-(4-halophenyl)-2,3-dihydrofuro-[2,3-d]pyrimidin-2-one analogues To a stirred solution of 5-iodo-2'-deoxyuridine (800 mg, 2.26 mmol) in anhydrous dimethylformamide (8 ml), was added diisopropylethylamine (584 mg, 0.8 ml, 4.52 mmol), the 4-n-alkoxy-phenylacetylene or 4-n-halo-phenylacetylene (6.76 mmol), tetrakis (triphenylphosphine) palladium (0) (261 mg, 0.266 mmol) and copper (I) iodide (86 mg, 0.452 mmol). The mixture was stirred for 18 hours, at room temperature, under a nitrogen atmosphere, after which time tlc (ethyl acetate/methanol 9:1), showed complete conversion of the starting material. Copper (I) iodide (80 mg, 0.40 mmol), triethylamine (15 ml) and methanol (20 ml) were then added to the mixture, which was subsequently refluxed for 4 hours. The reaction mixture was then concentrated in vacuo, and the resulting residue was dissolved in dichloromethane and methanol (1:1) (6 ml), and an excess of Amberlite IRA-400 (HC03-form) was added and stirred for 30 minutes. The resin was filtered and washed with methanol, and the combined filtrate was evaporated to dryness. The crude product was purified by flash column chromatography (initial eluent: ethyl acetate, followed by ethyl acetate/methanol (9:1). The appropriate fractions were combined and the solvent removed in vacuo, to give the pure product.

EXAMPLE 11

3-(2'-deoxy-β-D-ribofuranosyl)-6-(4-chlorophenyl)-[2,3-dihydrofuro-[2,3-d]pyrimidin-2-one

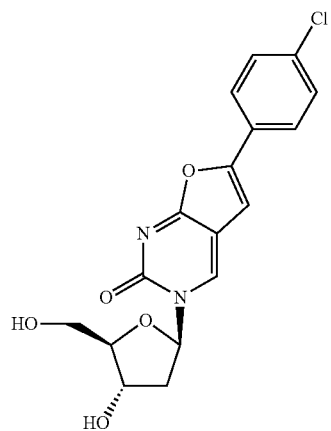 [SMILES: O=c1nc2oc(-c3ccc(Cl)cc3)cc2cn1[C@H]1C[C@H](O)[C@@H](CO)O1]

The procedure was carried out using 4-chlorophenylacetylene (0.92 g, 6.76 mmol which gave 3-(2'-deoxy-β-D-ribofuranosyl)-6-(4-chlorophenylacetylene)-2,3-dihydrofuro-[2,3-d]pyrimidin-2-one (474 mg, 58%), after purification by column chromatography.

$^1$H-NMR (d$_6$-DMSO; 300 MHz); 8.91 (1H, s, H-4), 7.88 (2H, H$_a$) –7.57 (2H, H$_b$) (AB system, $^3$J=7.89 Hz, $^4$J=2.3 Hz), 7.37 (1H, s, H-5), 6.19 (1H, dd, $^3$J=6.17 Hz, H1'), 5.35 (1H, d, $^3$J=4.1 Hz, 3'-OH), 5.24 (1H, t, $^3$J=5.12 Hz, 5'-OH), 4.26 (1H, m, H-3'), 3.95 (1H, m, H-4), 3.70 (2H, m, H-5'), 2.41 and 2.13 (2H, m, 2-H'a and 2-H'b). $^{13}$CNMR (d$_6$-DMSO; 75 MHz): 41.6 (C-2'), 60.9 (C-5'), 69.8 (C-3'), 88.0, 88.5, (C-1', C-4'), 100.8 (C-5), 107.0 (C-4a), 126.6 (C—Hb), 127.6 (ipso-C), 129.6 (C—Ha), 134.2 (C-4), 152.8 (para-C), 154.1 (C-6), 161.2 (C-2), 171.8 (C-7a). MS (ES) m/e 385 (MNa$^+$, 100%), 269 (baseNa$^+$,

EXAMPLE 12

3-(2'-deoxy-β-D-ribofuranosyl)-6-(4-bromophenyl)-2,3-dihydrofuro-[2,3-d]pyrimidin-2-one

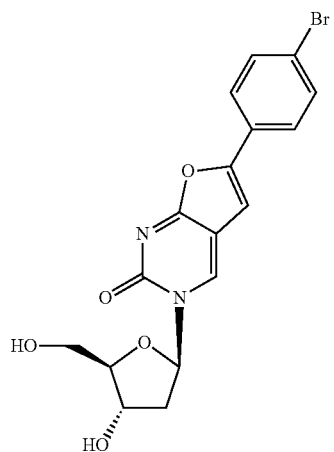 [SMILES: O=c1nc2oc(-c3ccc(Br)cc3)cc2cn1[C@H]1C[C@H](O)[C@@H](CO)O1]

The procedure was carried out using 4-bromophenylacetylene (1.22 g, 6.76 mmol), which gave 3-(2'-deoxy-β-D-ribofuranosyl)-6-(4-bromophenylacetylene)-2,3-dihydrofuro-[2,3-d]pyrimidin-2-one (174 mg, 19%), after purification by column chromatography.

$^1$H-NMR (d$_6$-DMSO; 300 MHz); 8.88 (1H, s, H-4), 7.78 (2H, H$_a$) –7.66 (2H, H$_b$) (AB system, $^3$J=7.89 Hz, $^4$J=2.3 Hz), 7.34 (1H, s, H-5), 6.14 (1H, dd, $^3$J=6.17 Hz, H1'), 5.31 (1H, d, $^3$J=4.1 Hz, 3'-OH), 5.19 (1H, t, $^3$J=5.12 Hz, 5'-OH), 4.65 (1H, m, H-3'), 3.92 (1H, m, H-4), 3.67 (2H, m, H-5'), 2.48 and 2.19 (2H, m, 2-H'a and 2-H'b). $^{13}$CNMR (d$_6$-DMSO; 75 MHz): 41.6 (C-2'), 60.9 (C-5'), 69.8 (C-3'), 88.1, 88.5, (C-1', C-4'), 100.9 (C-5), 107.0 (C-4a), 122.9 (C—Hb), 126.8 (Ipso-C), 127.9 (C—Ha), 139.0 (C-4), 152.8 (Para-C), 154.1 (C-6), 160.9 (C-2), 171.3 (C-7a). MS (ES$^+$) m/e 429 (MNa$^+$, 100%), 431 (MNa$^+$, 100%), 313 (baseNa$^+$, 25%), 315 (baseNa$^+$, 25%). Accurate mass: C$_{17}$H$_{15}$N$_2$O$_5$$^{79}$BrNa requires: 429.0062. found: 429.0061; C$_{17}$H$_{15}$N$_2$O$_5$$^{81}$BrNa requires 431.0042. found: 431.0052. Found: C, 49.89%; H, 3.88%; N, 6.63%. C$_{17}$H$_{15}$BrN$_2$O$_5$.0.5H$_2$O requires: C, 49.04%; H, 3.88%, N, 6.73%.

EXAMPLE 14

3-(2'-deoxy-β-D-ribofuranosyl)-6-(4-methoxyphenyl)-2,3-dihydrofuro-[2,3-d]pyrimidin-2-one

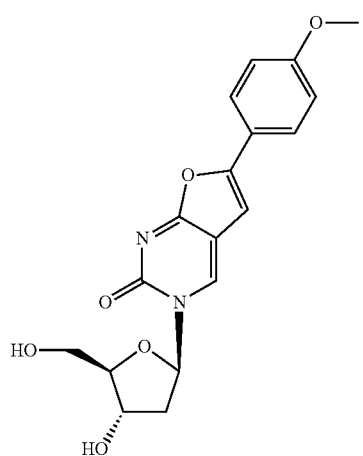 [SMILES: COc1ccc(-c2cc3cn([C@H]4C[C@H](O)[C@@H](CO)O4)c(=O)nc3o2)cc1]

The procedure was carried out using 4-methoxyphenylacetylene (0.893 g, 6.76 mmol), which gave 3-(2'-deoxy-β-D-ribofuranosyl)-6-(4-methoxyphenylacetylene)-2,3-dihydrofuro-[2,3-d]pyrimidin-2-one (353 mg, 43%), after purification by column chromatography.

$^1$H-NMR (d$_6$-DMSO; 300 MHz); 8.81 (1H, s, H-4), 7.77 (2H, H$_a$) –7.12 (2H, H$_b$) (AB system, $^3$J=7.89 Hz, $^4$J=2.3 Hz), 7.06 (1H, s, H-5), 6.20 (1H, dd, $^3$J=6.17 Hz, H1'), 5.32 (1H, d, $^3$J=4.1 Hz, 3'-OH), 5.20 (1H, t, $^3$J=5.12 Hz, 5'-OH), 4.05 (1H, m, H-3'), 3.93 (1H, m, H-4'), 3.83 (3H, s, OCH$_3$), 3.69 (2H, m, H-5'), 2.39 and 2.12 (2H, m, 2-H'a and 2-H'b). $^{13}$CNMR (d$_6$-DMSO; 75 MHz): 41.6 (C-2'), 55.7 (OCH$_3$), 61.0 (C-5'), 69.8 (C-3'), 88.5, 87.9 (C-1', C-4'), 97.7 (C-5), 107.5 (C-4a), 114.9 (C—Hb), 121.3 (ipso-C), 126.6 (C—Ha), 137.6 (C-4), 154.1 (para-C), 154.2 (C-6), 160.5 (C-2), 171.4 (C-7a). MS (ES$^+$) m/e 381 (MNa$^+$, 100%), 265 (baseNa$^+$, 20%), Accurate mass: C$_{18}$H$_{18}$N$_2$O$_6$Na requires: 381.1063. found: 381.1069. Found: C, 59.83%; H, 5.29%; N, 7.83%. C$_{18}$H$_{18}$N$_2$O$_6$ requires: C, 60.33%; H, 5.06%, N, 7.82%.

EXAMPLE 15

3-(2'-deoxy-β-D-ribofuranosyl)-6-(4-ethoxyphenyl)-2,3-dihydrofuro-[2,3-d]pyrimidin-2-one

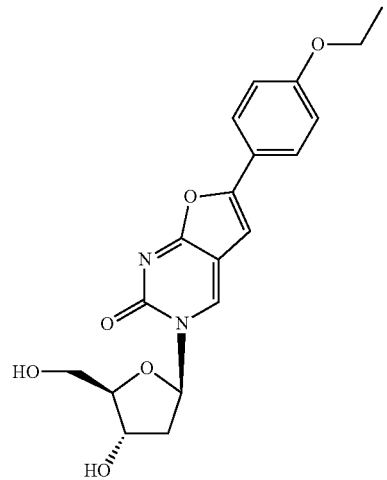 [SMILES: CCOc1ccc(-c2cc3cn([C@H]4C[C@H](O)[C@@H](CO)O4)c(=O)nc3o2)cc1]

The procedure was carried out using 4-ethoxyphenylacetylene (0.988 g, 6.76 mmol), which gave 3-(2'-deoxy-β-D-ribofuranosyl)-6-(4-ethoxyphenylacetylene)-2,3-dihydrofuro-[2,3-d]pyrimidin-2-one (256 mg, 30%), after purification by column chromatography.

$^1$H-NMR (d$_6$-DMSO; 300 MHz); 8.80 (1H, s, H-4), 7.77 (2H, H$_a$) –7.11 (2H, H$_b$) (AB system, $^3$J=7.89 Hz, $^4$J=2.3 Hz), 7.06 (1H, s, H-5), 6.19 (1H, dd, $^3$J=6.17 Hz, H1'), 5.32 (1H, d, $^3$J=4.1 Hz, 3'-OH), 5.20 (1H, t, $^3$J=5.12 Hz, 5'-OH), 4.26 (1H, m, H-3'), 4.08 (2H, q, OCH$_2$), 3.92 (1H, m, H-4), 3.69 (2H, m, H-5'), 2.40 and 2.09 (2H, m, 2-H'a and 2-H'b), 1.35 (3H, t, CH$_3$) $^{13}$CNMR (d$_6$-DMSO; 75 MHz): 14.9 (CH$_3$), 41.6 (C-2'), 61.0 (C-5'), 63.7 (OCH$_2$), 69.8 (C-3'), 87.9, 88.5, (C-1', C-4'), 97.6 (C-5), 107.5 (C-4a), 115.3 (C—Hb), 121.1 (ipso-C), 126.6 (C—Ha), 137.6 (C-4), 154.1 (para-C), 154.3 (C-6), 159.8 (C-2), 171.4 (C-7a). MS (ES$^+$) m/e 395 (MNa$^+$, 100%), 279 (baseNa$^+$, 20%). Accurate mass: C$_{19}$H$_{20}$N$_2$O$_6$Na requires: 395.1219. found: 395.1216. Found: C, 60.97%; H, 5.67%; N, 7.29%. C$_{19}$H$_{20}$N$_2$O$_6$ requires: C, 61.28%; H, 5.41%, N, 7.52%

EXAMPLE 16

3-(2'-deoxy-β-D-ribofuranosyl)-6-(4-n-propoxyphenyl)-2,3-dihydrofuro-[2,3-d]pyrimidin-2-one

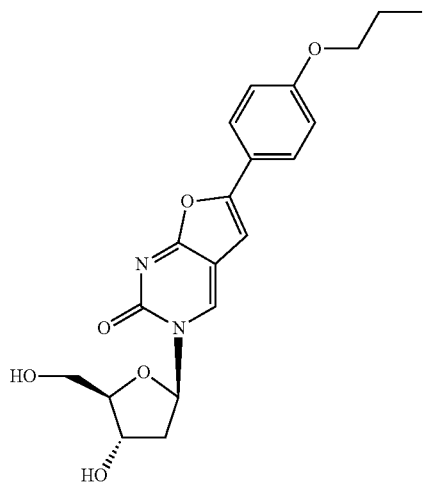 [SMILES: CCCOc1ccc(-c2cc3cn([C@H]4C[C@H](O)[C@@H](CO)O4)c(=O)nc3o2)cc1]

The procedure was carried out using 4-n-propoxyphenylacetylene (1.08 g, 6.76 mmol), which gave 3-(2'-deoxy-β-D-ribofuranosyl)-6-(4-n-propoxyphenylacetylene)-2,3-dihydrofuro-[2,3-d]pyrimidin-2-one (552 mg, 59%), after purification by column chromatography.

$^1$H-NMR (d$_6$-DMSO; 300 MHz); 8.80 (1H, s, H-4), 7.78 (2H, H$_a$) –7.12 (2H, H$_b$) (AB system, $^3$J=7.89 Hz, $^4$J=2.3 Hz), 7.07 (1H, s, H-5), 6.19 (1H, dd, $^3$J=6.17 Hz, H1'), 5.31 (1H, d, $^3$J=4.1 Hz, 3'-OH), 5.19 (1H, t, $^3$J=5.12 Hz, 5'-OH), 4.26 (1H, m, H-3'), 4.00 (2H, t, OCH$_2$), 3.98 (1H, m, H-4'), 3.67 (2H, m, H-5'), 2.40 and 2.12 (2H, m, 2-H'a and 2-H'b), 1.80 (2H, m, CH$_2$), 1.03 (3H, t, CH$_3$) $^{13}$CNMR (d$_6$-DMSO; 75 MHz): 10.7 (CH$_3$), 22.3 (CH$_2$), 41.6 (C-2'), 61.0 (C-5'), 69.5 (OCH$_2$), 69.8 (C-3'), 87.9, 88.5, (C-1', C-4'), 97.6 (C-5), 107.5 (C-4a), 115.4 (C—Hb), 121.1 (ipso-C), 126.6 (C—Ha), 137.6 (C-4), 154.1 (para-C), 154.3 (C-6), 160.0 (C-2), 171.3 (C-7a). MS (ES$^+$) m/e 409 (MNa$^+$, 100%), 293 (baseNa$^+$, 25%). Accurate mass: C$_{20}$H$_{22}$N$_2$O$_6$Na requires: 409.1376. found: 409.1374. Found: C, 61.97%; H, 5.67%; N, 7.29%. C$_{19}$H$_{20}$N$_2$O$_6$ requires: C, 62.17%; H, 5.74%, N, 7.25%.

EXAMPLE 17

3-(2'-deoxy-β-D-ribofuranosyl)-6-(4-n-pentoxyphenyl)-2,3-dihydrofuro-[2,3-d]pyrimidin-2-one

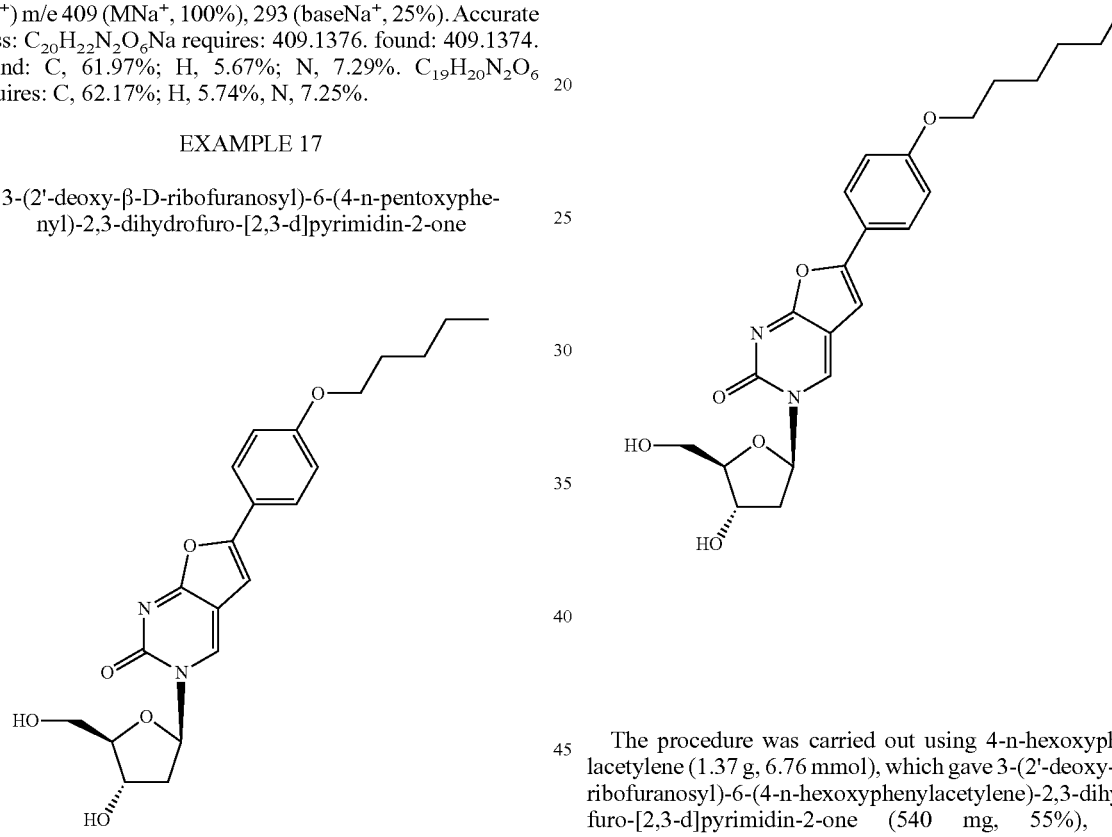

The procedure was carried out using 4-n-pentoxyphenylacetylene (1.27 g, 6.76 mmol), which gave 3-(2'-deoxy-β-D-ribofuranosyl)-6-(4-n-pentoxyphenylacetylene)-2,3-dihydrofuro-[2,3-d]pyrimidin-2-one (503 mg, 53%), after purification by column chromatography.

$^1$H-NMR (d$_6$-DMSO; 300 MHz); 8.80 (1H, s, H-4), 7.78 (2H, H$_a$) –7.07 (2H, H$_b$) (AB system, $^3$J=7.89 Hz, $^4$J=2.3 Hz), 7.04 (1H, s, H-5), 6.20 (1H, dd, $^3$J=6.17 Hz, H1'), 5.31 (1H, d, $^3$J=4.1 Hz, 3'-OH), 5.19 (1H, t, $^3$J=5.12 Hz, 5'-OH), 4.27 (1H, m, H-3'), 4.02 (2H, t, OCH$_2$), 3.93 (1H, m, H-4'), 3.69 (2H, m, H-5'), 2.39 and 2.13 (2H, m, 2-H'a and 2-H'b), 1.73 (2H, m, CH$_2$), 1.38 (4H, m, 2CH$_2$), 0.91 (3H, t, CH$_3$). $^{13}$CNMR (d$_6$-DMSO; 75 MHz): 14.3 (CH$_3$), 22.2 (CH$_2$CH$_3$), 28.0 (CH$_2$CH$_2$CH$_3$), 28.6 (CH$_2$CH$_2$CH$_2$CH$_3$) 41.6 (C-2'), 61.0 (C-5'), 68.0 (OCH$_2$), 69.8 (C-3'), 87.9, 88.5, (C-1', C-4'), 97.6 (C-5), 107.5 (C-4a), 115.4 (C—Hb), 121.1 (ipso-C), 126.6 (C—Ha), 137.6 (C-4), 154.1 (para-C), 154.3 (C-6), 160.0 (C-2), 171.4 (C-7a). MS (ES$^+$) m/e 437 (MNa$^+$, 100%), 321 (baseNa$^+$, 20%). Accurate mass: C$_{22}$H$_{26}$N$_2$O$_6$Na requires: 437.1689. found: 437.1695. Found: C, 60.07%; H, 6.63%; N, 6.27%. C$_{22}$H$_{26}$N$_2$O$_6$ 1.5H$_2$O requires: C, 59.85%; H, 6.62%, N, 6.35%.

EXAMPLE 18

3-(2'-deoxy-β-D-ribofuranosyl)-6(4-n-hexoxyphenyl)-2,3-dihydrofuro-[2,3-d]pyrimidin-2-one

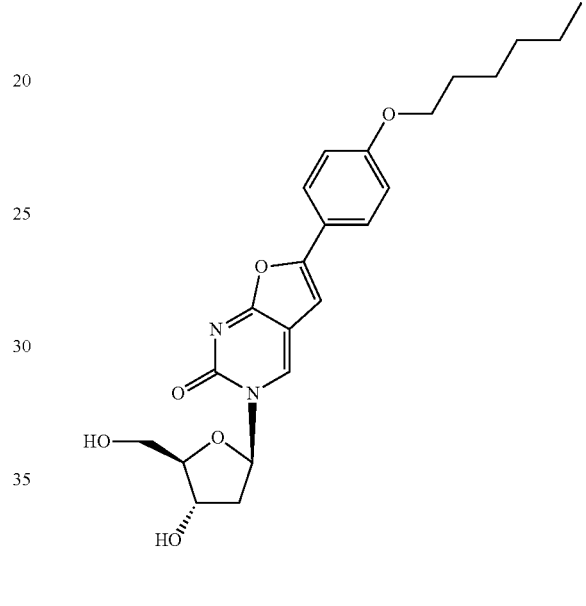

The procedure was carried out using 4-n-hexoxyphenylacetylene (1.37 g, 6.76 mmol), which gave 3-(2'-deoxy-β-D-ribofuranosyl)-6-(4-n-hexoxyphenylacetylene)-2,3-dihydrofuro-[2,3-d]pyrimidin-2-one (540 mg, 55%), after purification by column chromatography.

$^1$H-NMR (d$_6$-DMSO; 300 MHz); 8.80 (1H, s, H-4), 7.77 (2H, H$_a$) –7.11 (2H, H$_b$) (AB system, $^3$J=7.89 Hz, $^4$J=2.3 Hz), 7.07 (1H, s, H-5), 6.20 (1H, dd, $^3$J=6.17 Hz, H1'), 5.31 (1H, d, $^3$J=4.1 Hz, 3'-OH), 5.19 (1H, t, $^3$J=5.12 Hz, 5'-OH), 4.26 (1H, m, H-3'), 4.02 (2H, t, OCH$_2$), 3.94 (1H, m, H-4), 3.70 (2H, m, H-5'), 2.41 and 2.12 (2H, m, 2-H'a and 2-H' b), 1.73 (2H, m, OCH$_2$CH$_2$), 1.43 (2H, t, OCH$_2$CH$_2$CH$_2$), 1.32 (4H, m, 2CH$_2$), 0.89 (3H, t, CH$_3$). $^{13}$CNMR (d$_6$-DMSO; 75 MHz): 14.3 (CH$_3$), 22.4 (CH$_2$CH$_3$), 25.5 (CH$_2$CH$_2$CH$_3$), 28.9 (CH$_2$CH$_2$CH$_2$CH$_3$), 31.3 (CH$_2$CH$_2$CH$_2$CH$_2$CH$_3$), 41.6 (C-2'), 60.9 (C-5'), 68.0 (OCH$_2$), 69.8 (C-3'), 88.0, 88.5, (C-1', C-4'), 100.8 (C-5), 107.0 (C-4a), 115.3 (C—Hb), 121.1 (ipso-C), 126.6 (C—Ha), 137.5 (C-4), 154.2 (para-C), 154.5 (C-6), 161.2 (C-2), 171.8 (C-7a). MS (ES$^+$) m/e 451 (MNa$^+$, 100%), 335 (baseNa$^+$, 10%). Accurate mass: C$_{23}$H$_{28}$N$_2$O$_6$Na requires: 451.1845. found: 451.1843. Found: C, 64.28%; H, 6.74%; N, 6.35%. C$_{23}$H$_{28}$N$_2$O$_6$ requires: C, 64.47%; H, 6.59%, N, 6.54%.

EXAMPLE 19

3-(2'-deoxy-β-D-ribofuranosyl)-6-(4-n-heptoxyphenyl)-2,3-dihydrofuro-[2,3-d]pyrimidin-2-one

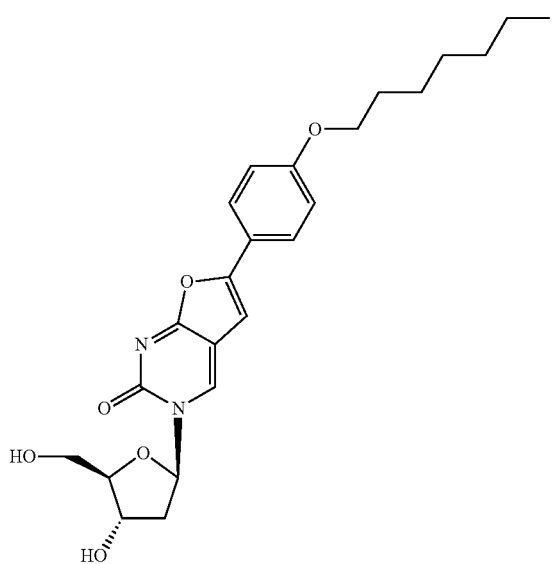 [SMILES: CCCCCCCOc1ccc(-c2cc3cn([C@H]4C[C@H](O)[C@@H](CO)O4)c(=O)nc3o2)cc1]

The procedure was carried out using 4-n-heptoxyphenylacetylene (1.46 g, 6.76 mmol), which gave 3-(2'-deoxy-β-D-ribofuranosyl)-6-(4-n-heptoxyphenylacetylene)-2,3-dihydrofuro-[2,3-d]pyrimidin-2-one (193 mg, 19%), after purification by column chromatography.

$^1$H-NMR (d$_6$-DMSO; 300 MHz); 8.80 (1H, s, H-4), 7.78 (2H, H$_a$) –7.11 (2H, H$_b$) (AB system, $^3$J=7.89 Hz, $^4$J=2.3 Hz), 7.07 (1H, s, H-5), 6.20 (1H, dd, $^3$J=6.17 Hz, H1'), 5.31 (1H, d, $^3$J=4.1 Hz, 3'-OH), 5.19 (1H, t, $^3$J=5.12 Hz, 5'-OH), 4.26 (1H, m, H-3'), 4.02 (2H, t, OCH$_2$), 4.00 (1H, m, H-4'), 3.92 (2H, m, H-5'), 2.51 and 2.09 (2H, m, 2-H'a and 2-H'b), 1.73 (2H, m, OCH$_2$CH$_2$), 1.33 (8H, m, 4-CH$_2$), 0.87 (3H, t, CH$_3$). 13CNMR (d$_6$-DMSO; 75 MHz): 14.3 (CH$_3$), 22.4 (CH$_2$CH$_3$), 25.8 (CH$_2$CH$_2$CH$_3$), 28.8 (CH$_2$CH$_2$CH$_2$CH$_3$), 31.6 (CH$_2$CH$_2$CH$_2$CH$_2$CH$_3$), 33.7 (CH$_2$CH$_2$CH$_2$CH$_2$CH$_2$CH$_3$), 41.6 (C-2'), 61.2 (C-5'), 68.8 (OCH$_2$), 69.8 (C-3'), 88.1, 88.7, (C-1', C-4'), 99.7 (C-5), 107.0 (C-4a), 115.3 (C—Hb), 121.1 (ipso-C), 126.8 (C—Ha), 137.5 (C-4), 154.2 (para-C), 154.5 (C-6), 161.2 (C-2), 171.8 (C-7a). MS (ES$^+$) m/e 465 (MNa$^+$, 100%), 349 (baseNa$^+$, 10%). Accurate mass: C$_{24}$H$_{30}$N$_2$O$_6$Na requires: 465.2002. found: 465.2001. Found: C, 62.74%; H, 7.08%; N, 6.06%. C$_{24}$H$_{30}$N$_2$O$_6$.H$_2$O requires: C, 62.59%; H, 7.01%, N, 6.08%.

10%). Accurate mass: C$_{17}$H$_{15}$N$_2$O$_5$ClNa requires: 385.0567. found: 385.0575. Found: C, 56.02%; H, 4.39%; N, 7.67%. C$_{17}$H$_{15}$ClN$_2$O$_5$ requires: C, 56.29%; H, 4.17%, N, 7.72%.

Biological Activity

The compounds of each the present examples 1 to 19 were tested in vitro in tissue culture assays for potent anti-viral action with respect to varicella zoster virus (VZV). The results in terms of EC50 which was defined as the drug concentration (in yM) required to reduce virus-induced cytopathicity by 50%, are given in the Table below. The column titles in the table stand for:

R$_9$, for compounds embodying the present invention, is Ar as in formula I above.

EC50 VZV OKA yM stands for "50% effective concentration" and is the compound concentration required to reduce viral plaque formation after 5 days by 50%, compared to an untreated control, using OKA viral strain.

EC50 VZV YS AM stands for "50% effective concentration" and is the compound concentration required to reduce viral plaque formation after 5 days by 50%, compared to untreated control, using YS viral strain.

EC50 VZV TK'07 M stands for "50% effective concentration" and is the compound concentration required to reduce viral plaque formation after 5 days by 50%, compared to untreated control, using viral strain 07; TK deficient.

EC50 VZV TK-YS uM stands for "50% effective concentration" and is the compound concentration required to reduce viral plaque formation after 5 days by 50%, compared to untreated control, using viral strain YS; TK deficient.

MCC AM is the minimum cytotoxic concentration to human embryonic lung cells.

CC50 AM is 50% cytotoxic concentration to human embryonic lung cells.

Further details of the methodology employed can be found in McGuigan et al. J. Med. Chem., 1999, 42, 4479-4484.

TABLE

| Example | R | EC50 VZV OKA μM | EC50 VZV YS μM | EC50 VZV TK-07 μM | EC50 VZV TK-YS μM | MCC μM | CC50 μM |
|---|---|---|---|---|---|---|---|
| 7 | —C$_6$H$_5$ | <0.5 | <0.5 | >200 | 162 | >200 | >200 |
| 8 | —pC$_6$H$_4$—CH$_3$ | <0.5 | <0.5 | 103 | >200 | >200 | >200 |
| 9 | —pC$_6$H$_4$—C$_2$H$_5$ | <0.5 | <0.5 | >50 | >50 | 200 | 123 |
| 1 | —pC$_6$H$_4$—nC$_3$H$_7$ | 0.011 | 0.009 | >50 | >20 | ≥50 | 188 |
| 2 | —pC$_6$H$_4$—nC$_4$H$_9$ | 0.0032 | 0.0002 | 13 | >20 | | |
| 3 | —pC$_6$H$_4$—nC$_5$H$_{11}$ | 0.00006 | 0.00005 | >20 | >5 | | |
| 4 | —pC$_6$H$_4$—nC$_6$H$_{13}$ | 0.00011 | 0.00007 | >5 | >5 | | |
| 5 | —pC$_6$H$_4$—nC$_7$H$_{15}$ | 0.0034 | 0.0009 | >5 | >5 | 5 | 18 |
| 6 | —pC$_6$H$_4$—nC$_8$H$_{17}$ | 0.015 | 0.005 | >20 | >20 | ≥20 | >200 |
| Acyclovir | | 2.9 | 1 | 74 | 125 | >200 | >200 |
| BVDU | | | 0.003 | | | | |
| Ex2 WO 98/49177 | —nC$_{10}$H$_{21}$ | 0.015 | 0.008 | >50 | >50 | >50 | >50 |
| 10 | —pC$_6$H$_4$—F | >50 | >50 | >50 | >50 | 200 | 171 |
| 11 | —pC$_6$H$_4$—Cl | 0.1 | 0.08 | >20 | >20 | ≥20 | >200 |
| 12 | —pC$_6$H$_4$—Br | 0.29 | 0.2 | >5 | >5 | >2 | 96 |
| 13 | —pC$_6$H$_4$—C$_6$H$_4$ | 0.031 | 0.032 | >5 | >5 | >200 | >200 |
| 14 | —pC$_6$H$_4$—OCH$_3$ | 0.05 | 0.05 | >50 | >50 | 200 | >200 |

TABLE-continued

| Example | R | EC50 VZV OKA μM | EC50 VZV YS μM | EC50 VZV TK-07 μM | EC50 VZV TK-YS μM | MCC μM | CC50 μM |
|---|---|---|---|---|---|---|---|
| 15 | —pC$_6$H$_4$—OC$_2$H$_5$ | 0.01 | 0.01 | 50 | >50 | 200 | >200 |
| 16 | —pC$_6$H$_4$—OnC$_3$H$_7$ | 0.002 | 0.002 | 11 | >50 | ≥200 | >200 |
| 17 | —pC$_6$H$_4$—OnC$_5$H$_{11}$ | 0.002 | 0.002 | 3.7 | >20 | >50 | >200 |
| 18 | —pC$_6$H$_4$—OnC$_6$H$_{13}$ | 0.002 | 0.002 | >5 | >20 | >20 | >200 |
| 19 | —pC$_6$H$_4$—OnC$_7$H$_{15}$ | 0.002 | 0.002 | >50 | >20 | ≥50 | >200 |

As can be seen from the data contained in the above Table, compounds comprising Examples 2 to 5 and 15 to 19 embodying the present invention demonstrate increased potency having regard to the known potency of the prior art compounds contained in the Table. Optimum compounds can be seen to those of Examples 2 to 5 and 16 to 19 exemplifying the present invention. Compounds displaying the greatest increase in potency can be seen to be those of Examples 3 and 4 of the present invention.

Increased potency of the compounds of the present invention permit effective reduced doses to be administered to a patient in need thereof. Reduced dosage, either in terms of the number of doses required or the quantity required per dose or both, can enhance the convenience to, and hence compliance by, the patient and can permit a commensurate reduction in likely host toxicity and any side effects.

Compounds comprising Examples 1, 6 and 11 to 14 demonstrate comparable potency having regard to the known potency of the prior art compounds contained in the Table.

What is claimed is:

1. A compound having the formula:

$$(I)$$

wherein
Ar is an aromatic ring system, the aromatic ring system comprising one six-membered aromatic ring and one substituent at the para position on the six-membered aromatic ring and wherein the substituent is selected from the group consisting of unsubstituted aryl, chlorine, and bromine;
R$_8$ and R$_9$ are each independently selected from the group consisting of hydrogen, alkyl, cycloalkyl, halogen, amino, alkylamino, dialkylamino, nitro, cyano, alkoxy, aryloxy, thiol, alkylthiol, arylthiol, and aryl;
Q is selected from the group consisting of O, S and CY$_2$, wherein Y is the same or different and is selected from H, alkyl, and halogen;
X is selected from the group consisting of O, NH, S, N-alkyl, (CH$_2$)$_m$, wherein m is 1 to 10, and CY$_2$ wherein Y is the same or different and is selected from hydrogen, alkyl and halogen;
Z is selected from the group consisting of O, S, NH, and N-alkyl;
U''' is H and U' is selected from H and CH$_2$T, or U' and U'' are joined so as to form a ring moiety including Q wherein U'—U'' together is respectively selected from the group consisting of —CTH-CT'T''— and —CT'=CT'-, so as to provide ring moieties selected from the group consisting of:

wherein:
T is selected from the group consisting of OH, H, halogen, O-alkyl, O-acyl, O-aryl, CN, NH$_2$ and N$_3$;
T' is selected from the group consisting of H and halogen and, wherein when more than one T' is present, they are the same or different;
T'' is selected from the group consisting of H and halogen; and
W is selected from the group consisting of H, a phosphate group and a pharmacologically acceptable salt thereof;
with the provisos that:
(1) when T is OAc and T' and T'' are present and are H, Ar is not 4-(2-benzoxazolyl)phenyl; and
(2) when Q, X and Z are each O, and R$_8$, R$_9$, T', T'' and W are each H and T is OH or O-acyl, Ar is:
one six-membered carbocyclic aromatic ring substituted by one or more moieties independently selected from the group consisting of alkyl, aryl, cycloalkyl, chlorine, bromine, iodine, cyano, alkylamino, dialkylamino, alkoxy, aryloxy, alkylthio and arylthio, any of which alkyl, cycloalkyl or aryl moieties is substituted by one or more members selected from the group consisting of chlorine, bromine, iodine, CN, CO$_2$alkyl (C$_1$ to C$_6$), CONH$_2$, CONH alkyl (C$_1$ to C$_6$), SR, S alkyl (C$_1$ to C$_6$) and NO$_2$;
one six-membered aromatic ring system which contains one, two, three or four hetero atoms and which ring system is optionally substituted; or
two fused six-membered aromatic rings, which is optionally substituted.

2. A method for preparing compounds according to claim 1 wherein a 5-halo nucleoside analogue is contacted with a terminal alkyne in the presence of a catalyst, or a 5-alkynyl nucleoside is cyclized in the presence of a catalyst.

3. A method of treatment of a Varicella Zoster Virus (VZV) viral infection comprising administering to a patient in need of such treatment an effective dose of a compound having the formula:

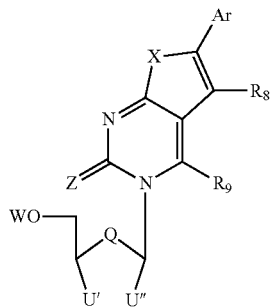

(I)

wherein

Ar is an aromatic ring system, the aromatic ring system comprising one six-membered aromatic ring and one substituent at the para position on the six-membered aromatic ring and wherein the substituent is selected from the group consisting of unsubstituted aryl, chlorine, and bromine;

$R_8$ and $R_9$, are each independently selected from the group consisting of hydrogen, alkyl, cycloalkyl, halogen, amino, alkylamino, dialkylamino, nitro, cyano, alkoxy, aryloxy, thiol, alkylthiol, arylthiol, and aryl;

Q is selected from the group consisting of O, S and $CY_2$, wherein Y is the same or different and is selected from H, alkyl and halogen;

X is selected from the group consisting of O, NH, S, N-alkyl, $(CH_2)_m$ wherein m, is 1 to 10, and $CY_2$ wherein Y is the same or different and is selected from hydrogen, alkyl and halogen;

Z is selected from the group consisting of O, S, NH, and N-alkyl;

U" is H and U' is selected from H and $CH_2T$, or U' and U" are joined so as to form a ring moiety including Q wherein U'—U" together is respectively selected from the group consisting of —CTH-CT'T" and —CT'=CT'-, so as to provide ring moieties selected from the group consisting of:

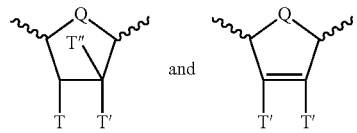

T is selected from the group consisting of OH, H, halogen, O-alkyl, O-acyl, O-aryl, CN, $NH_2$ and $N_3$;

T' is selected from the group consisting of H and halogen and, wherein when more than one T' is present, they are the same or different;

T" is selected from the group consisting of H and halogen; and

W is selected from the group consisting of H, a phosphate group and a pharmacologically acceptable salt thereof.

4. A pharmaceutical composition comprising a compound according to claim 1 and a pharmaceutically acceptable excipient.

5. A composition comprising a compound having the formula:

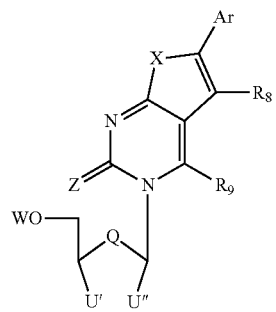

(I)

wherein

Ar is an aromatic ring system, the aromatic ring system comprising one six-membered aromatic ring and one substituent at the para position on the six-membered aromatic ring and wherein the substituent is selected from the group consisting of unsubstituted aryl, chlorine, and bromine;

$R_8$ and $R_9$ are each independently selected from the group consisting of hydrogen, alkyl, cycloalkyl, halogen, amino, alkylamino, dialkylamino, nitro, cyano, alkoxy, aryloxy; thiol, alkylthiol, arylthiol, and aryl;

Q is selected from the group consisting of O, S and $CY_2$, wherein Y is the same or different and is selected from H, alkyl and halogen;

X is selected from the group consisting of O, NH, S, N-alkyl, $(CH_2)_m$ wherein m is 1 to 10, and $CY_2$ wherein Y is the same or different and is selected from hydrogen, alkyl and halogen;

Z is selected from the group consisting of O, S, NH, and N-alkyl;

U" is H and U' is selected from H and $CH_2T$, or U' and U" are joined so as to form a ring moiety including Q wherein U'—U" together is respectively selected from the group consisting of —CTH-CT'T" and —CT'=CT'-, so as to provide ring moieties selected from the group consisting of:

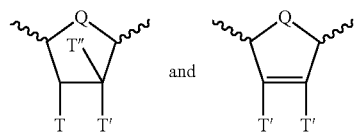

wherein:

T is selected from the group consisting of OH, H, halogen, O-alkyl, O-acyl, O-aryl, CN, $NH_2$ and $N_3$;

T' is selected from the group consisting of H and halogen and, wherein more than one T' is present, they are the same or different;

T" is selected from the group consisting of H and halogen; and

W is selected from the group consisting of H, a phosphate group and a pharmacologically acceptable salt thereof;

with the proviso that when T is OAc and T' and T" are present and are H, Ar is not 4-(2-benzoxazolyly)phenyl, in combination with a pharmaceutically acceptable excipient.

6. A method of preparing a pharmaceutical composition comprising the step of combining a compound having the formula:

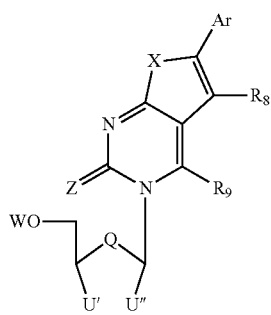

(I)

wherein
Ar is an aromatic ring system, the aromatic ring system comprising one six-membered aromatic ring and one substituent at the para position on the six-membered aromatic ring and wherein the substituent is selected from the group consisting of unsubstituted aryl, chlorine, and bromine;
$R_8$ and $R_9$ are each independently selected from the group consisting of hydrogen, alkyl, cycloalkyl, halogen, amino, alkylamino, dialkylamino, nitro, cyano, alkoxy, aryloxy, thiol, alkylthiol, arylthiol, and aryl;
Q is selected from the group consisting of O, S and $CY_2$, wherein Y may be the same or different and is selected from H, alkyl and halogen;
X is selected from the group consisting of O, NH, S, N-alkyl, $(CH_2)_m$ wherein in is 1 to 10, and $CY_2$ wherein Y is the same or different and is selected from hydrogen, alkyl and halogen;
Z is selected from the group consisting of O, S, NH, and N-alkyl;
U" is H and U' is selected from H and $CH_2T$, or U' and U" are joined so as to form a ring moiety including Q wherein U'—U" together is respectively selected from the group consisting of —CTH-CT'T" and —CT'=CT'-, so as to provide ring moieties selected from the group consisting of:

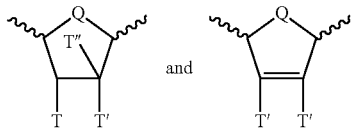

wherein:
T is selected from the group consisting of OH, H, halogen, O-alkyl, O-acyl, O-aryl, CN, $NH_2$ and $N_3$;
T' is selected from the group consisting of H and halogen and, wherein more than one T' is present, they may be the same or different;
T" is selected from the group consisting of H and halogen; and
W is selected from the group consisting of H, a phosphate group and a pharmacologically acceptable salt thereof;
with the proviso that when T is OAc and T' and T" are present and are H, Ar is not 4-(2-benzoxazolyly)phenyl,
with a pharmaceutically acceptable excipient.

7. A compound selected from the group consisting of:
3-(2'-deoxy-β-D-ribofuranosyl)-6-(4-chlorophenyl)-2,3-dihydrofuro-[2,3-d]pyrimidin-2-one;
3-(2'-deoxy-β-D-ribofuranosyl)-6-(4-bromophenyl)-2,3-dihydrofuro-[2,3-d]pyrimidin-2-one; and
3-(2'-deoxy-β-D-ribofuranosyl)-6-(4-phenylphenyl)-2,3-dihydrofuro-[2,3-d]pyrimidin-2-one.

* * * * *